United States Patent [19]

Grandi et al.

[11] Patent Number: 5,869,278
[45] Date of Patent: Feb. 9, 1999

[54] PROCESS FOR THE PREPARATION OF MATURE HUMAN GROWTH HORMONE BY ENZYMATIC HYDROLYSIS OF A SOLUBLE PRECURSOR WITH IMMOBILIZED FACTOR XA

[75] Inventors: Guido Grandi, Milan; Giuliano Galli, Rome, both of Italy

[73] Assignee: Eniricerche S.p.A., Milan, Italy

[21] Appl. No.: 203,662

[22] Filed: Feb. 28, 1994

Related U.S. Application Data

[63] Continuation of Ser. No. 858,228, Mar. 26, 1992, abandoned.

[30] Foreign Application Priority Data

Mar. 28, 1991 [IT] Italy ................................. MI91A0861

[51] Int. Cl.⁶ ............................. C12P 21/06; C12N 11/02; C12N 11/10; A61K 38/27; C07K 14/475
[52] U.S. Cl. ......................... 435/68.1; 435/174; 435/177; 435/178; 530/399; 930/120
[58] Field of Search ..................... 435/174, 176, 435/177, 178, 179, 180, 181; 530/399; 930/120

[56] References Cited

U.S. PATENT DOCUMENTS 5,047,333  9/1991  Grandi et al. .......................... 435/68.1

FOREIGN PATENT DOCUMENTS 0211288  2/1987  European Pat. Off. .
0321940  6/1989  European Pat. Off. .
9111454  8/1994  WIPO .

OTHER PUBLICATIONS

Maugh (1984) *Science*, 223, 474–476, Guilbault et al. (1979) *Acts. Chem. Res.*, 12, 344–350.
Imai et al. (1986) *J. Biochem*, 100(2), 425–432.
Takashi Imai et al., Journal of Biochemistry, 100, No. 2 (6038), Aug. 1986, "Synthesis and Characterization of Human Prorenin in *Esherichia coli* ", Tokyo, Japan, pp. 425–432.
Sylvia Ellinger et al., Journal of Clinical Microbiology, May, 1989, "Cleavage of Procaryotically Expressed Human Immunodeficiency Virus Fusion Proteins by Factor $X_3$ and Application in Western Blot (Immunoblot) Assays", pp. 971–976.

*Primary Examiner*—David M. Naff
*Assistant Examiner*—Jon P. Weber
*Attorney, Agent, or Firm*—Rogers & Wells

[57] ABSTRACT

Mature Human Growth Hormone is prepared by enzymatic hydrolysis of a soluble precursor with immobilized Factor Xa. The soluble precursor contains a cleavage recognition sequence, Ile—Glu—Gly—Arg, for Factor Xa. The Factor Xa is preferably immobilized on CNBr activated Sepharose Cl-4B containing cyclic imido carbonate groups. Immobilization is carried out by reaction of amine groups on Factor X with the cyclic imido carbonate groups of the CNBr activated Sepharose Cl-4B to form covalently immobilized Factor X, which is then activated to Factor Xa with a protein contained in Russell's viper venom (RVV) in the presence of $Ca^{++}$ ions.

1 Claim, 4 Drawing Sheets

110' 90' 60' 30' 0'

PROCESS FOR THE PREPARATION OF MATURE HUMAN GROWTH HORMONE BY ENZYMATIC HYDROLYSIS OF A SOLUBLE PRECURSOR WITH IMMOBILIZED FACTOR XA

This application is a continuation of application Ser. No. 07/858,228, filed Mar. 26, 1992, now abandoned.

The present invention relates to an improved process for the preparation of mature polypeptides by the enzymatic hydrolysis of soluble precursors therefor with Factor Xa immobilised on a solid insoluble support.

Recombinant DNA techniques are known in the art for the preparation of polypeptides fused to an aminoacid sequence which can be divided specifically in vitro by enzymatic hydrolysis.

In particular, a method has been described for the preparation of the mature (191 aminoacids) human growth hormone (hGH) from soluble precursors therefore by (hydrolysis of the precursors with the enzyme Factor Xa (EP-A-321940).

In accordance with this method, the enzymatic hydrolysis is carried out by the addition of Factor Xa to the proteic solution containing the precursor for the purified hGH and the separation of the mature hGH thus obtained from the reaction mixture.

However, this method has disadvantages resulting from the use of Factor Xa in solution such as, for example, the need to remove the enzyme and its degradation products or any contaminants of animal origin at the end of the reaction, an operation which requires troublesome procedures for the separation and purification of the mature product.

It is in fact known that Factor Xa is not very stable in solution at ambient temperature and degrades to form fragments which can be difficult to separate from the mature product.

It has now been found that it is possible to overcome the disadvantages mentioned above by immobilising the Factor Xa on a solid insoluble support in such a manner as to preserve its enzymatic specificity and by using this active support in the hydrolysis of the soluble precursor for the desire product.

Hence, the subject of the present invention is an improved process for the preparation of mature polypeptides by the enzymatic hydrolysis of soluble precursors therefor with Factor Xa immobilised on a solid insoluble support.

More particularly, the method of the present invention includes:

a) immobilising Factor Xa on a solid insoluble support in such a manner as not to alter the specificity of the enzyme;

b) bringing the active support into contact with the proteic solution containing the soluble precursor for the desired polypeptide, the precursor having the sequence X—Ile—Glu—Gly—Arg—Y where:

X is Met or a peptide capable of conferring solubility on the precursor;

(SEQ ID No. 1) Ile—Glu—Gly—Arg is the tetrapeptide recognised by Factor Xa;

Y is a mature polypeptide, c) recovering the mature polypeptide at the end of the hydrolysis reaction;

d) re-utilising the immobilised Factor Xa for subsequent enzymatic hydrolysis reactions.

The immobilisation of the enzyme on the solid support may be effected by one of the known techniques such as, for example, covalent bonding with or without a space between the reactive groups of the enzyme and those of the support, ionic bonding and physical adsorption.

The Factor Xa is preferably immobilised on a solid support activated by means of a covalent bond.

Examples of solid supports suitable for the purpose of the present invention may be selected from natural polymers, possibly modified, synthetic polymers or inorganic mineral supports available commercially and either already activated or for activation before the immobilisation.

More particularly, the support sold by Pharmacia as CNBr activated "Sepharose Cl-4B", which is covalently cross-linked agarose gel beads which have been activated by CNBr to contain cyclic imido carbonate groups, was used for the method of the present invention.

The Factor Xa is immobilised by the reaction of one or more amine groups present on the enzyme with the cyclic imidocarbonate present on the support, giving derivatives of the type:

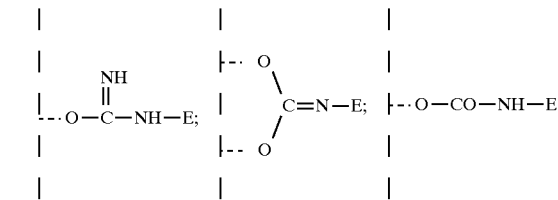

The immobilisation of Factor Xa is effected by placing the activated support in contact with the enzyme in a buffer at a pH of between 7.0 and 9.0, preferably between 7.5 and 8.0.

The contact times are those needed for the completion of the bonding reaction between the enzyme and the reactive groups of the support.

At the end of the reaction, the support is washed repeatedly with the buffer to avoid any reactive groups still remaining on the support.

In a further embodiment of the method of the present invention, Factor X is immobilised on the solid insoluble support and then it is activated to give Factor Xa with a protein contained in Russell's viper venom (RVV) in the presence of $Ca^{++}$ ions. The support thus obtained is enzymatically active.

The enzymatic hydrolysis reaction is carried out by feeding the solution containing the precursor into a column packed with the active support. The pH of the proteic solution is between 6.0 and 9.0, preferably between 7.5 and 8.5.

The concentration of the precursor is selected in such a manner as to give the maximum productivity per unit time. Generally the concentration of the precursor is between 2.0 mg/ml and 30.0 mg/ml.

The degree of conversion is checked at time intervals so as to enable the reaction to be stopped at the desired conversion.

This check is carried out by FPLC (Fast Protein Liquid Chromatography) analysis of samples of the reaction mixture with the use of an anionic exchange analytical column, for example, the Mono-Q HR 5/5 (Pharmacia), in conditions which allow the precursor to be separated from the mature protein.

The reaction mixture is recovered from the column by displacement with a buffer at a pH of about 8.0 until the proteins have completely disappeared from the eluate.

The use of the immobilised enzyme simplifies the production of the mature product, minimises the probability of contamination with the enzyme or its autolysis products and other proteins of animal origin, enables the repeated use of the same support and the possibility of stopping the hydrolysis of the precursor at the desired moment.

Figure 1:
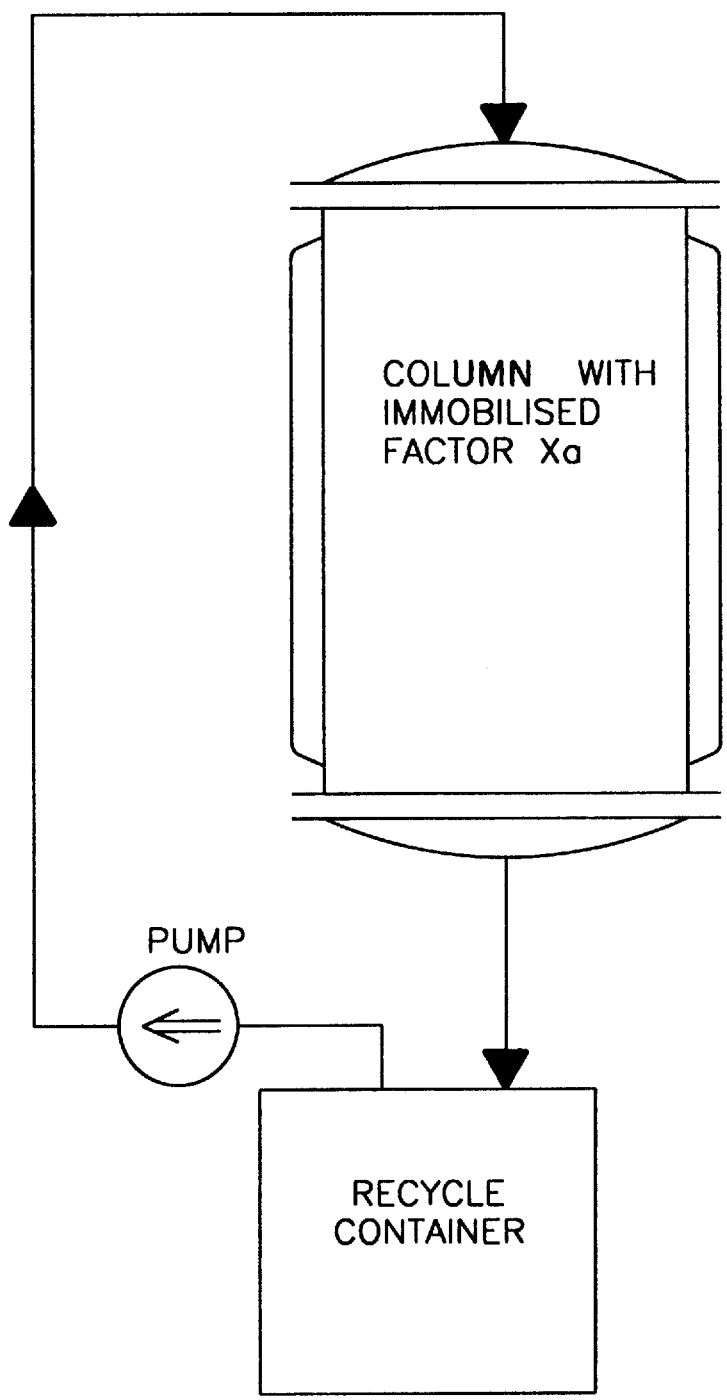
FIG. 1 Diagrammatic production of hGH by hydrolysis of the precursor with Factor Xa immobilised on a solid insoluble support.

The experimental examples which follow are illustrative and non limiting of the present invention.

EXAMPLE 1

Immobilisation of Factor Xa 5 g of Sepharose® CL-4B activated with CNBr (Pharmacia) previously washed in a glass filter funnel (90–150μ) with one liter of 1N HCl and with 0.5 liters of 0.1M NaHCO$_3$ were introduced into a 300 ml glass vessel. To the support were then added 100 ml of a 0.1M NaHCO$_3$ solution containing 53 mg of Factor Xa. The suspension was kept under agitation (200 rpm) at ambient temperature (20°–25° C.) for thirty minutes and then for 1 night at 4° C.

The active support was then washed in a glass filter funnel (90/150μ) with 500 ml of 0.1M NaHCO$_3$, then for at least two hours with 500 ml of 0.2M Tris-HCl at pH 8.0 containing 0.5M NaCl in order to block any reactive groups still present on the support. Washing was then carried out with a further 500 ml of 20 mM Tris-HCl at pH 8.0, 0.1M NaCl, and kept at 4° C. until the moment of use. Alternatively, in order to avoid the danger of polution, the support may be kept in 0.02% NaN$_3$ and then washed repeatedly before use.

EXAMPLE 2

Hydrolysis of the Precursor for hGH With the Immobilised Factor Xa 80 ml of a solution containing 8 mg/ml of the soluble precursor (SEQ ID No. 2) Met—Glu—Glu—Leu—Met—Ile—Glu—Gly—Arg—hGH in 20 mM Tris-HCl, 0.1M NaCl, pH 8.0 buffer were subjected to enzymatic hydrolysis with the use of Factor Xa immobilised as described in Example 1. The solution was recycled through 1.6×18 cm column containing the insoluble Factor Xa with a flow of 50 ml/cm$^2$. During the loading and before the start of the recycling, a quantity of eluate equal to 75% of the volume of the column was thrown away to avoid dilution of the reaction mixture with the liquid in the column itself. The degree of conversion achieved was then checked at time intervals so as to enable the enzymatic reaction to be stopped at the desired moment. This check was effected by FPLC (Fast Protein Liquid Chromatography) analysis of samples of the reaction mixture, with the use of the analytical column Mono-Q HR 5/5 (Pharmacia), with the following operative conditions:

Flow=2 ml/minute

Buffer A=20 mM Tris/Acetate+10 mM NaCl, pH 7.0

Buffer B=20 mM Tris/Acetate+80 mM NaCl, pH 5.0

After the sample has been loaded, a gradient (20 ml) from 0=a 50% of the buffer B in the buffer A is applied to the column. The run is then continued (from 20 to 24 ml) in isocratic conditions and then, still in isocratic conditions, there is supplied 100% of the buffer B (from 24–27 ml). The percentage of the buffer B is then brought from 100% to 0% (from 27 to 29 ml) and then the cycle is terminated, the column being re-equilibrated with the buffer A (from 29–36 ml). At this point the column is ready for a new test.

The method allows both the hormone and the precursor to be separated and determined.

After the desired degree of conversion has been reached, the reaction mixture is recovered from the column by displacement with 20 mM Tris-HCl, 0.1M NaCl, pH 8.0 until the protein has completely disappeared from the eluate, as determined with the BIORAD kit.

Figure 2:
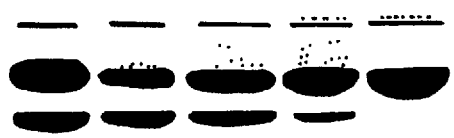
FIG. 2 Electrophoretic examination of the samples taken at different times from the recycle container during the hydrolysis of the precursor to hGH.
Figure 3A:
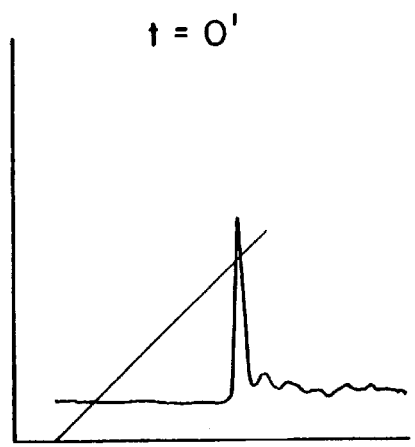
FIGS. 3A–3E Elutograms obtained by FPLC on the samples of reaction mixture given in FIG. 2.
Figure 3B:
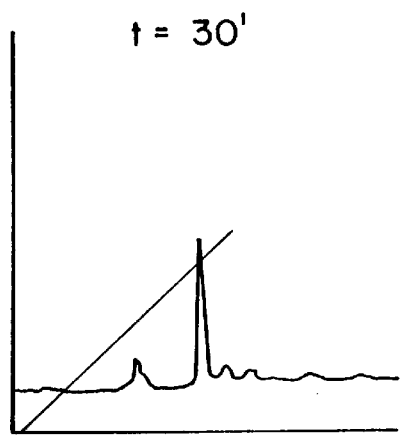
Figure 3C:
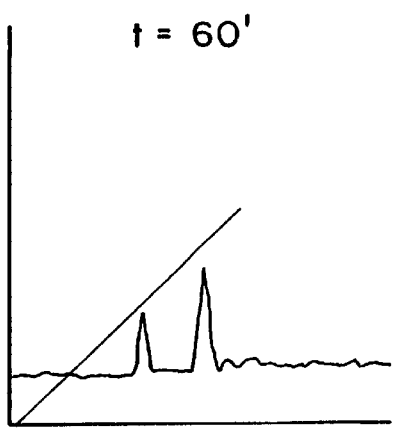
Figure 3D:
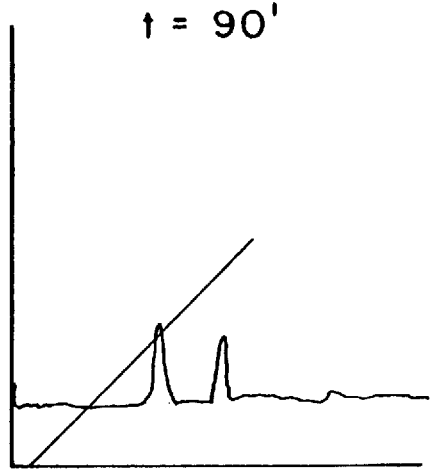
Figure 3E:
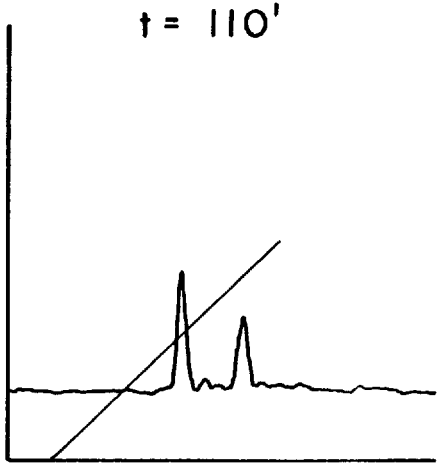

FIG. 2 shows the results of the electrophoretic examination of the samples taken at various times from the recycling container (FIG. 1); FIG. 3 shows the corresponding elutograms obtained by FPLC.

As may be seen in both FIGS. (2 and 3) a conversion of the precursor to the mature form of the hormone is observed with the passage of time.

The Factor Xa immobilised on the support was used several times without any appreciable falling off in its activity being noted.

EXAMPLE 3

Immobilisation of Factor X and its Activation to Factor Xa 5 g of Sepharose® CL-4B activated with CNBr (Pharmacia) previously washed in a glass filter funnel (90–150μ) with one liter of 1N HCl and with 0.5 liters of 0.1M NaHCO$_3$ were introduced into a 300 ml glass vessel. To the support were then added 100 ml of a 0.1M NaHCO$_3$ solution containing 60 mg of Factor X. This suspension was kept under agitation (200 rpm) at ambient temperature (20°–25° C.) for thirty minutes and then for one night at 4° C.

This support on which the Factor X was immobilised was then washed in a glass filter funnel (90–150μ) with 500 ml of 0.1M NaHCO$_3$ and subsequently for at least two hours with 500 ml of 0.2M Tris-HCl, pH 8.0, 0.5M NaCl in order to block any reactive groups still present on the support. The support was then washed again with 500 ml of 20 mM Tris-HCl, pH 8.0, 0.1M NaCl and then packed into a 1.6×18 cm column.

The Factor X was activated to Factor Xa by recycling a solution of RVV (2 mg/ml) in 20 mM Tris-HCl, pH 8.0, +1 mM CaCl$_2$ in the same column. After four hours of recycling at ambient temperature, the column was washed repeatedly with 20 mM Tris-HCl, pH8.0, 0.5M NaCl until the proteins had disappeared completely from the eluate. The support thus obtained was used for the hydrolysis of the soluble pre-cursor for hGH as described in Example 2 above. The results obtained show that the solid insoluble support is active on the fused protein confirming the activation of the Factor X to Factor Xa.

We claim:

1. A process for the preparation of mature human growth hormone comprising enzymatic hydrolysis with immobilized Factor Xa of a soluble precursor of said hormone, said precursor having the sequence X—Ile—Glu—Gly—Arg—Y, wherein X is Met or a peptide which confers solubility on the precursor; Ile—Glu—Gly—Arg is the tetrapeptide recognized by Factor Xa; and Y is the mature human growth hormone, and wherein the Factor Xa is immobilized on CNBr activated "Sepharose Cl-4B", which is covalently cross-linked agarose gel beads which have been activated by CNBr to contain cyclic imido carbonate groups, which immobilization occurs by reaction of amine groups on Factor X with the cyclic imido carbonate groups of the CNBr activated Sepharose Cl-4B to form covalently immobilized Factor X, which is then activated to Factor Xa with a protein contained in Russell's viper venom (RVV) in the presence of $Ca^{++}$ ions.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 4 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 1:

Ile   Glu   Gly   Arg
    1

( 2 ) INFORMATION FOR SEQ ID NO: 2:

( i ) SEQUENCE CHARACTERISTICS:
        ( A ) LENGTH: 9 amino acids
        ( B ) TYPE: amino acid
        ( C ) STRANDEDNESS:
        ( D ) TOPOLOGY: linear ( i i ) MOLECULE TYPE: peptide ( x i ) SEQUENCE DESCRIPTION: SEQ ID NO: 2:

Met   Glu   Glu   Leu   Met   Ile   Gly   Gly   Arg
    1                             5